United States Patent
Shams et al.

(10) Patent No.: US 10,846,599 B2
(45) Date of Patent: *Nov. 24, 2020

(54) COLLABORATION OF AUDIO SENSORS FOR GEO-LOCATION AND CONTINUOUS TRACKING OF HEALTH CONDITIONS FOR USERS IN A DEVICE-INDEPENDENT ARTIFICIAL INTELLIGENCE (AI) ENVIRONMENT

(71) Applicant: Lumin, LLC, San Jose, CA (US)

(72) Inventors: Nima Lahijani Shams, San Jose, CA (US); Suhas Maheshaiah, San Jose, CA (US); Laila Wahdan, San Jose, CA (US)

(73) Assignee: LUMIN, LLC, San Jose, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/806,249

(22) Filed: Nov. 7, 2017

(65) Prior Publication Data

US 2018/0144255 A1    May 24, 2018

Related U.S. Application Data

(60) Continuation-in-part of application No. 15/360,444, filed on Nov. 23, 2016, now Pat. No. 9,830,554, which is a division of application No. 15/266,497, filed on Sep. 15, 2016, now Pat. No. 9,818,061, which is a continuation-in-part of application No. 14/521,450, filed on Oct. 22, 2014, now Pat. No. 9,710,753.

(Continued)

(51) Int. Cl.
*G06N 5/02* (2006.01)
*G10L 17/04* (2013.01)
*G10L 17/06* (2013.01)
*G10L 15/22* (2006.01)
*G10L 25/66* (2013.01)
*G10L 17/00* (2013.01)

(52) U.S. Cl.
CPC .............. *G06N 5/022* (2013.01); *G10L 15/22* (2013.01); *G10L 17/04* (2013.01); *G10L 17/06* (2013.01); *G10L 25/66* (2013.01); *G10L 17/00* (2013.01)

(58) Field of Classification Search
CPC ......... G06N 5/022; G10L 14/22; G10L 17/04; G10L 17/06; G10L 25/66; G10L 17/00
See application file for complete search history.

(56) References Cited

U.S. PATENT DOCUMENTS

| | | | |
|---|---|---|---|
| 7,223,781 B2 | 5/2007 | Dannhardt et al. | |
| 7,663,502 B2 | 2/2010 | Breed | |

(Continued)

*Primary Examiner* — Robert A Cassity
*Assistant Examiner* — Tsu-Chang Lee
(74) *Attorney, Agent, or Firm* — Law Office of Dorian Cartwright; Dorian Cartwright

(57) ABSTRACT

Audio sensors collaborate for geo-location and tracking of health conditions for multiple users. Different users can be independently geo-located and tracked within the AI environment. Location is determined from two or more AI clients of known locations that detect an event such as a human voice command to connect a call with a specific user. Responsive to classification of a health event of concern, in view of the estimated location, a command for an AI action, such as contacting a hospital server or adapting to monitor a suspected health condition, is received for a response to the health event at the AI clients that detected the health event, or others.

16 Claims, 13 Drawing Sheets

Related U.S. Application Data

(60) Provisional application No. 61/896,651, filed on Oct. 28, 2013, provisional application No. 61/901,436, filed on Nov. 7, 2013, provisional application No. 61/894,383, filed on Oct. 22, 2013.

(56) References Cited

U.S. PATENT DOCUMENTS

| | | |
|---|---|---|
| 2003/0228035 A1 | 12/2003 | Parunak et al. |
| 2004/0024851 A1 | 2/2004 | Naidoo et al. |
| 2014/0207721 A1 | 7/2014 | Filson et al. |
| 2014/0226855 A1 | 8/2014 | Savvides et al. |
| 2014/0266669 A1 | 9/2014 | Fadell et al. |
| 2014/0277769 A1 | 9/2014 | Matsuoka et al. |
| 2015/0018979 A1 | 1/2015 | Tomii et al. |

COLLABORATION OF AUDIO SENSORS FOR GEO-LOCATION AND CONTINUOUS TRACKING OF HEALTH CONDITIONS FOR USERS IN A DEVICE-INDEPENDENT ARTIFICIAL INTELLIGENCE (AI) ENVIRONMENT

CROSS-REFERENCE TO RELATED APPLICATIONS

This application claims priority as a continuation-in-part to U.S. application Ser. No. 15/360,444 filed Nov. 23, 2016, entitled ESTABLISHING AUDIO CONNECTIONS BETWEEN USERS BEING CONTINUOUSLY TRACKED BY COLLABORATIVE SENSORS, which is a divisional of U.S. application Ser. No. 15/266,497 filed Sep. 15, 2016, entitled COLLABORATION OF AUDIO SENSORS FOR GEO-LOCATION AND CONTINUOUS TRACKING OF MULTIPLE USERS IN A DEVICE-INDEPENDENT ARTIFICIAL INTELLIGENCE (AI) ENVIRONMENT, which is a continuation-in-part to U.S. application Ser. No. 14/521,450, filed Oct. 22, 2014, entitled COLLABORATION OF AUDIO SENSORS FOR GEO-LOCATION OF EVENTS IN AN ARTIFICIAL INTELLIGENCE (AI) ENVIRONMENT, by Shams et al., which claims the benefit of priority to U.S. Application No. 61/894,383, filed Oct. 22, 2013, entitled HOME/OFFICE ARTIFICIAL INTELLIGENCE (AI) USING EMBEDDED SENSORS, by Shams et al., Application No. 61/896,651, filed Oct. 28, 2013, entitled COLLABORATION OF SENSORS IN AN ARTIFICIAL INTELLIGENCE (AI) ENVIRONMENT, by Shams et al., and also claims priority to Application No. 61/901,436, filed Nov. 7, 2013, entitled COMMANDING CLOUD-BASED APPLICATIONS FROM AN ARTIFICIAL INTELLIGENCE (AI) ENVIRONMENT USING CONSUMER ELECTRONIC DEVICES, by Shams et al., the contents of each being hereby incorporated by reference in its entirety.

FIELD OF THE INVENTION

The invention relates generally, to computer software, and more specifically, to a collaboration of audio sensors in an artificial intelligence (AI) environment to identify and continuously track health conditions of users at different locations amongst the audio sensors.

BACKGROUND

Home AI refers to various levels of automation for appliances and electronics in homes, businesses, automobiles, and other environments. Many conventional systems provide low levels of automation, and are closed to a predefined list of commands. For example, a coffee maker can be programmed to brew coffee at a certain time, lights in the home can be turned on automatically due to low lighting conditions, and power to electronics can be "clapped" on or "clapped" off. Also, smoke detectors and thermostats can perform certain actions based on certain direct instructions.

With the addition of networking, home automation devices can send alerts through a network. For instance, a conventional security system or fire detection system can send alerts through a network because of an intrusion or fire emergency, respectively. Other types of automation operate according to voice commands when a button is pushed to activate the voice command mode, such as on smartphones and in automobiles.

Problematically, conventional home AI fails to distinguish between multiple users in a common environment, at the same time. In some conventional systems, commands are processed without any voice analysis, thereby treating all users together as a single user. In other conventional systems, a user is logged in, so commands are processed as all coming from a single identified user. The lack of identification limits personalization levels for AI interactions in conventional systems. But it is inconvenient, and unnatural, in a multi-user environment for users to constantly identify themselves.

Conventional AI in for health situations also falls short. Many health alert systems require user interaction from a bracelet or voice command. One drawback is that user interaction is explicit. Another drawback is dependency upon hardware devices to be worn by users (e.g., the bracelet). In a more general context, smartphone-based AI (e.g., Siri by Apple Computers of Cupertino, Calif.) and other hardware are device dependent, relying upon users carrying around and intentionally interacting with the smartphone or a specific piece of hardware.

Another smartphone-based AI that relies upon users carrying around a physical device is location services. A user is assumed to be located proximate to the device which provides a location using GPS coordinates of the device.

What therefore is needed is a robust technique that monitors health conditions, without explicit user interaction. The technique should locate and track multiple users within a device-independent AI environment. Location information should enable continuous tracking of health conditions over different locations and feedback in real-time and at a specific location, within the device-independent AI environment.

SUMMARY

To meet the above-described needs, methods, computer program products, and systems for monitoring health conditions for users with a collaboration of audio sensors for geo-location and tracking of multiple users in a device-independent artificial intelligence (AI) environment (e.g., home, office, outdoor area, or business).

In one embodiment, location information is stored for each of the plurality of geographically-dispersed AI clients. Each of the AI clients can include an audio sensor, a network controller, and a feedback mechanism (e.g., a speaker or an LED) within a common enclosure. Responsive to detection of a health event (e.g., coughing, sneezing, snoring, walking), or other type of event (e.g., involving a human, machine, or ambient condition) at two or more of the plurality of geographically-dispersed AI clients, audio event data is centrally received from audio sensors of the two or more of the plurality of geographically-dispersed AI sensors.

An audio event is classified as a health audio event, in one embodiment, by comparing the audio event data (or series of audio event data) against parameters of one or more specific health concerns associated with the user. Each health concern can be expressed as a mathematical model with parameters. Health concerns can be diagnosed or monitored through AI clients of a home automation system.

Different users can be independently geo-located and tracked within the AI environment. Identification data can be applied to events to distinguish one user from another, including voice prints, habits, walking patters, and the like. As users move around an AI environment, new events are detected at new AI clients, which are processed to update location. A location of users involved in a call is estimated based on the location information and the audio event data (e.g., triangulation). Responsive to classification of the event in view of the estimated location, a command for an AI action, such as connecting a call between users, is received for a response to the event at the AI clients that detected the event, or others.

Advantageously, the user experience with AI is more natural because the AI is not dependent on users carrying around a device for location-based AI interactions.

BRIEF DESCRIPTION OF THE DRAWINGS

In the following drawings, like reference numbers are used to refer to like elements. Although the following figures depict various examples of the invention, the invention is not limited to the examples depicted in the figures.

DETAILED DESCRIPTION

Figure 1A:
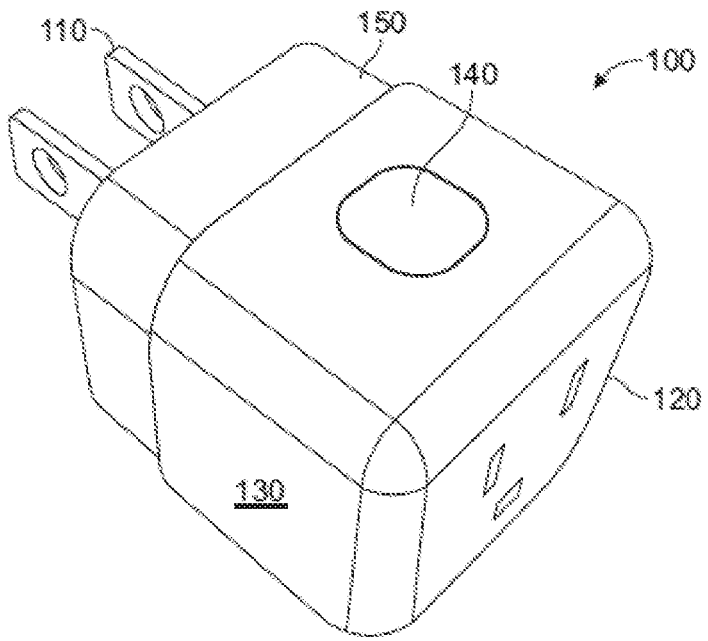
FIGS. 1A and 1B are schematic diagrams illustrating perspective views of an artificial appliance (AI) appliance, according to one embodiment.

To meet the above-described needs, methods, computer program products, and systems for collaboration of audio sensors for geo-location of events in an artificial intelligence (AI) environment monitoring health conditions for users with a collaboration of audio sensors for geo-location and tracking of multiple users in a device-independent artificial intelligence (AI) environment (e.g., home, office, outdoor area, or business).

Many other embodiments are possible, and although not explicitly set forth for the sake of brevity, are within the scope of the present disclosure.

I. Overview of Features

The scalable AI, command-control system is an adaptive AI that can learn the habits of one or more individuals and one or more environments for location-based monitoring of health conditions for the one or more individuals. As a result, actions taken by the AI system become more accurate over time. Microphones and speakers distributed in consumer appliances around the home allow natural voice interaction without a physical device needing to be worn or held. Each consumer appliance can also be outfitted with a feedback mechanism, such as an LED light, a speaker, a buzzer or display, and even feedback on a separate device. Other sensors on consumer appliances can collect data about the household for storage in a database.

Advantageously, users can perform normal tasks around the home as the present AI system tracks patterns and learns behaviors to automatically make those tasks easier using prediction algorithms (e.g., automatic lighting based on user movements, detection and notification of house activity via SMS). Exceptions to predicted actions can raise red flags (e.g., identification of medical emergency). Users can interface with the AI system by talking naturally for hands-free control and management for non-automated voice commands and interactions (e.g., lights come one automatically, and user requests a certain color or intensity as a modification). The AI system acts as an assistant (e.g., notifying user of incoming calls or guests). Users can retrieve public and personal information from the cloud (e.g., sports scores, bank account balances, Facebook statuses, etc.), make purchases (e.g., using Amazon.com APIs), enter new calendar appointments (e.g., using Google.com APIs for calendar application), and the like.

The system can also provide feedback to users. Sounds and lights can confirm commands and communicate modes of the system (e.g., voice response stating "your order will be delivered Friday" or green blinking LED). In some embodiments, once a central processor analyzes information from several locations to identify a health condition, and provides feedback through to a current location (e.g., an audio reminder about current sugar intake in relation to a potential diabetes health condition for a user upon detection that the user has entered the kitchen).

For example, as users normally proceed throughout a household, AI clients distributed around the household analyze sounds from the user and other interactions to raise potential health conditions. Health conditions, as referred to herein, includes physical and/or mental issues, such as, but not limited to, the flu, diabetes, bi polar disorder, passive aggressiveness, spinal and back pain conditions, trip and fall, heart attack, stroke, ADHD, depression, (attention deficit hyperactive disorder), and the like. Health conditions are referred to in a diagnostic manner by tracking symptoms, as well as being referred to in a preventative manner by warning against certain activities.

The system can constantly track and monitor various activities of the user that are not direct health conditions but can be indicators of such. To this end, system can track how active is a user, how much they laugh, cough, cry, sleep, snore and move around a bed. Bathroom habits, eating habits, social habits, and even sex life can be taken as factors for health conditions. Changes in voice, or other patterns can be indicative of a health condition. Thus, some events in isolation are benign and not considered a relevant to a health condition, but when the same events are considered in combination within a time period or geographical location, a health condition may be apparent (e.g., late night eating as a habit, cough and sneeze regularly observed while in the presence of a cat or dog).

Home automation, as referred to throughout the description, should be understood to be an exemplary environment. Other environments include offices, automobiles, business, wearables, parking lots, shopping malls, gyms, libraries, hybrid environments, multi-system environments, and the like. Consumer appliances and electronics refer to just a few categories of devices that can be manufactured for, or retrofitted to plug in to, the AI system. Also, users can be owners of the systems, or employees, guests, customers or others that interact with the systems of others.

The examples of this description are merely illustrative and are not intended to be limiting as one of ordinary skill in the art will recognize many variations consistent with the spirit of the inventions as specifically described herein.

II. Health Monitoring System Using Distributed AI Clients

Figure 1B:
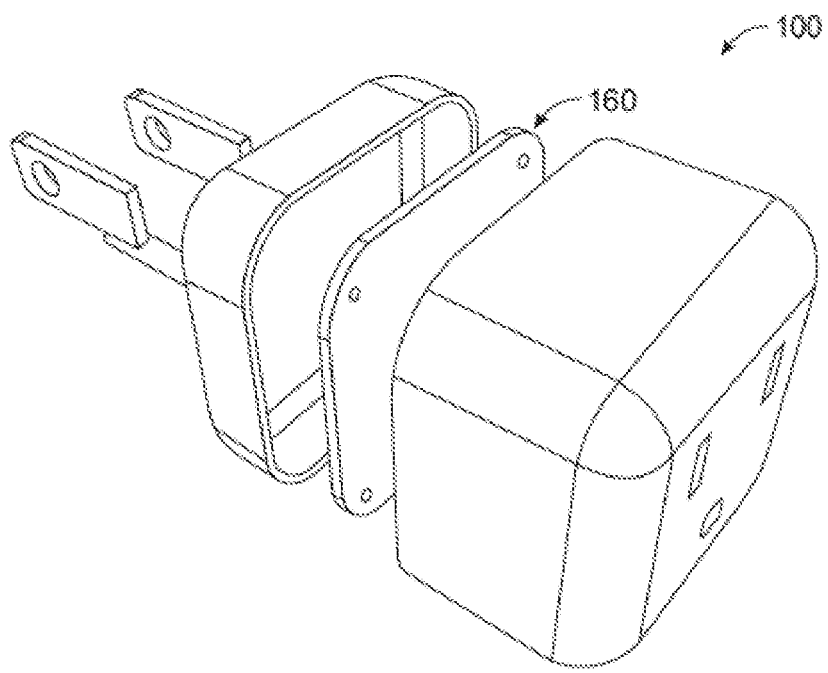

FIGS. 1A and 1B are schematic diagrams illustrating perspective views of an AI appliance 100 in the form of wall outlets, according to one embodiment. The AI appliance 100 modifies a traditional wall outlet to a provide AI with a plug 110 for insertion into an electrical outlet receptacle at one end and a receptacle 120 for an electrical appliance, to be controlled by the AI appliance 100, to plug in to an opposite end. An enclosure 130 can be composed of plastic, rubber, or any appropriate material. A button 140 on a top side of the enclosure allows manual controls such as power on, power off, and reset. A colored portion 150 of the enclosure covers an LED light to give a user visual feedback to events detected by sensors. Some AI appliances modify existing traditional appliances (e.g., over wall outlet as 100) while others integrate existing traditional appliances (e.g., in wall outlet installed into the drywall (not shown)).

An exploded view of the AI appliance 100 in FIG. 1B exposes a motherboard or printed circuit board (PCB) 160 used to implement AI circuitry. Sensors, a transceiver, antennae, a central processing unit (CPU), a power supply and/or power controller, memory element, or other electronic components can be attached to the board (see e.g., FIG. 2). Many other types of appliances can be AI appliances as described herein.

In the case of calls between users, the AI appliance 100 is one of many sensors distributed around an AI environment. The AI appliance 100 can detect events used in collaboration with other appliances to geo-locate the users. The AI appliance 100 can also provide a microphone and a speaker for conducting calls in collaboration with other appliances. Many different applications can be implemented on the geo-location platform, conducting geo-location enabled calls between multiple users is just one of those applications.

Figure 2:
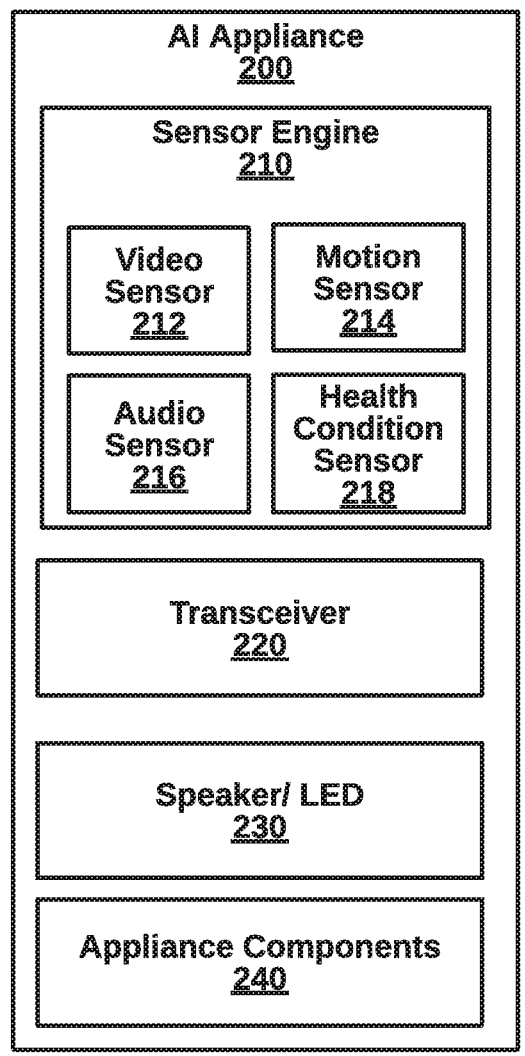
FIG. 2 is a more detailed block diagram illustrating components of an AI appliance, according to one embodiment.

FIG. 2 is a block diagram illustrating an AI appliance 200 (or AI client), according to one embodiment. A sensor engine 210 collects raw data that is analyzed by a centralized AI server, at times in aggregation with raw data collected at other locations. The present embodiment includes a video sensor 212, a motion sensor 214, an audio sensor 216 (e.g., a microphone for conducting a telephone call), an ambient light sensor and a health condition sensor 215. The health condition sensor 215 can be any specialized sensor that plugs into a general-purpose chassis of the sensor engine 210, can be downloaded and executed on a processor, or both. For instance, a heartbeat detector can be installed locally while a doctor sends commands to a central server to configure the health condition sensor 218 accordingly.

More, generally, the sensors continually collect data in a temporary memory, in one embodiment, that can be framed and transmitted as a file upon detecting an event (e.g., MP3 file or MP4 file). The present configurations of sensor are merely illustrative and can be implementation-specific. Other types of sensors include temperature sensors, humidity sensors, gas detectors and other ambient condition sensors. The AI appliance 200 can be implemented with both analog and digital electronic components, including conventional components such as a processor and other components necessary for operation (see FIG. 10).

A transceiver 220 transmits the raw data collected by sensors to a centralized AI server and/or other external resources. Complementary software components can be provided such as IP protocol stack software. The transceiver 220 can operate in accordance with protocols, such as Wi-Fi, Bluetooth, 3G or 4G, an electrical outlet protocol, or any other type of wireless communication standard. Optionally, a Bluetooth 4.2 or other type of radio can provide Bluetooth beacon tracking to assist in location determination.

A speaker/LED 230 allows the system to provide feedback to users for AI actions. Additionally, speakers output sound for telephone calls or multimedia playback. Computer generated voices can ask questions concerning predicted actions or respond with confirmations of an event. An action with one AI appliance 200 can be confirmed with feedback at a different AI appliance 200 responsive to movement, location of user, or feedback capability (e.g., an AI appliance with a speaker may take over feedback if the initiating AI appliance only has an LED light and voice feedback is preferred). Alternatively, the confirming action initiated by one user may concern a different user that is detected at a different location. Numerous forms of chirping, blinking, and the like can be implemented.

Appliance components 240 can be any traditional components for operations for the appliance. For an AI refrigerator, the appliance components 240 include a condenser and fan. For a wall component, the appliance components 240 include a receptor and terminals circuit connections. In some cases, the appliance components 240 have feedback to the AI components for functions such as power consumption monitoring, on/off toggling, and the like. In some embodiments, a traditional appliance is converted to an AI appliance, for example, by using an outlet that is an AI appliance.

Figure 3A:
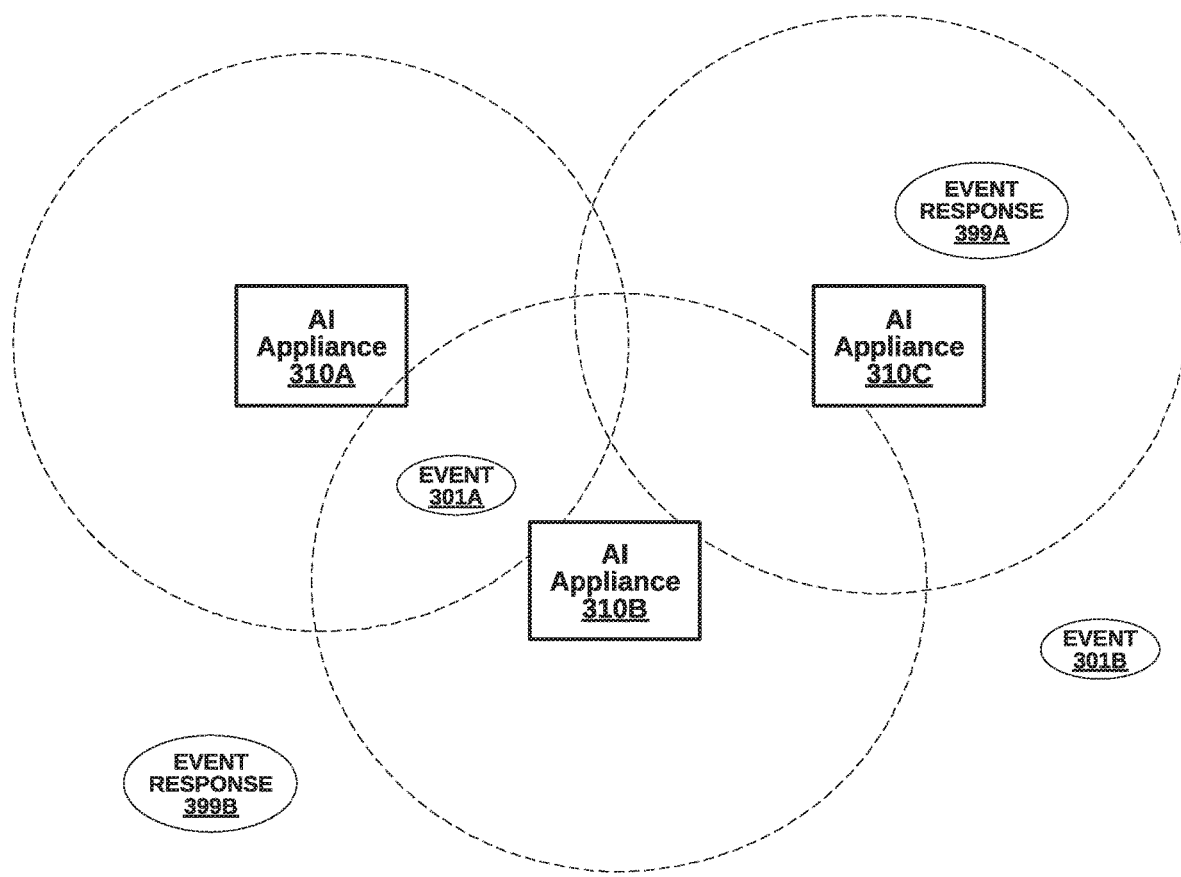
FIG. 3A is a block diagram illustrating AI appliances coordinated for providing home automation, according to one embodiment.

FIG. 3A is a block diagram illustrating a system 300 with AI appliances 310A-C coordinated for providing home automation, according to one embodiment.

Event 301 occurs at a location in an AI environment within range of sensors on AI appliance 310A and AI appliance 310B. Events can originate from human commands, human activities, machine activities, ambient conditions, or the like. As a result, more than one AI appliance collects sensor data for analysis. In one embodiment, the analysis geo-locates event 301 based on sound intensity and known locations of sensors. With a third sensor located at a third location, the accuracy increases as the third input allows a triangulation of sound intensity. In another embodiment, motion sensors or video cameras are used for geo-location. In other embodiments, chemical analysis and other ambient measurements are taken at different locations for analysis.

Event response 399A and 399B occurs, in this embodiment, at a location distinct from events 301A and 301B, respectively. For example, a user enters a home at event 301 and a coffee machine (e.g., plugged into AI appliance 310C) turned on at event response 399. Alternatively, event response 399A and 399B, as well as events 301A and B, can take place at other locations.

Figure 3B:
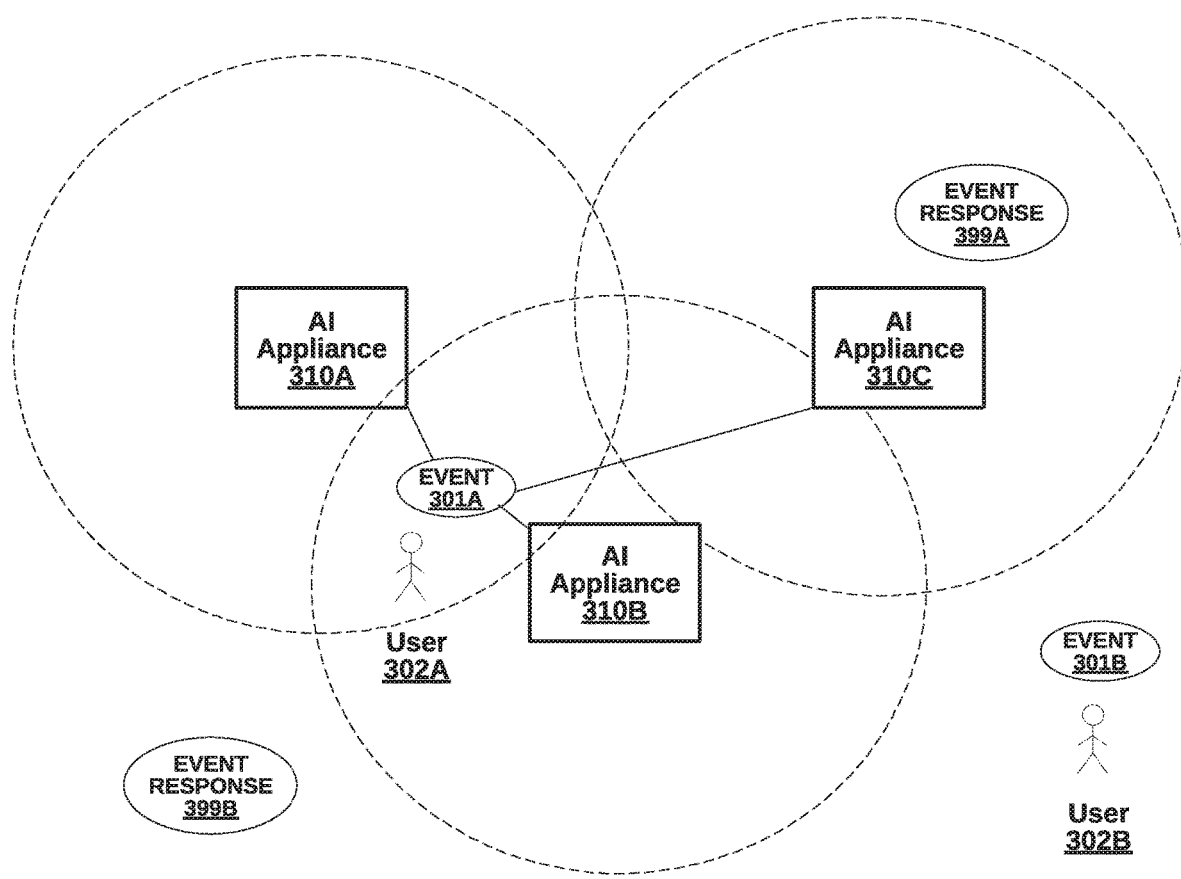
FIG. 3B is a block diagram illustrating how AI appliances locate a user event, according to an embodiment.

One example of an event and event response occurs in the context of establishing a call between users. As shown in FIG. 3B, user 302A and user 302B are located in the AI environment, as defined by AI appliances 301A-C. User 302A issues an audio command such as "Call Laila" as event 301A. Both AI appliance 310A and 310B are within audio range of user 302B, so both pick up the voice command. Volume (or intensity) is one factor that can be used to determine whether user A 302A is close to AI appliance 310A or 310B. A third AI appliance would allow for triangulation for a more precise location. AI appliance 310C may pick up trace audio for use in triangulations, but some sounds may below a required threshold for use. Additionally, more than three data points may be available.

Besides location triangulation, multiple microphones can pick up the same voice command. The additional samples from different locations, in combination, help isolate a higher quality A last known location of user 302B may already be known from event 301B, which could be a direct interaction or an observed action such as washing dishes. The last known location can be used as an initial contact attempt to user B 302B as an event response. One or more AI appliances proximate to event 301B can call out Laila's name to confirm or update location. Once located, a call is connected between users 302A and 302B. One embodiment balances speaker and/or microphone volumes on AI appliances based on user location. As either location changes, speaker and/or microphone volumes can be rebalanced, as a response.

In some embodiments, location can refer to a location of digital activity, for example, a location can be an SMS application, a social networking web site, smartphone location coordinates, or anywhere that a user can be reached. For instance, an SMS message can be sent to a user with a link to connect to a call conducted by an AI controller.

Figure 4A:
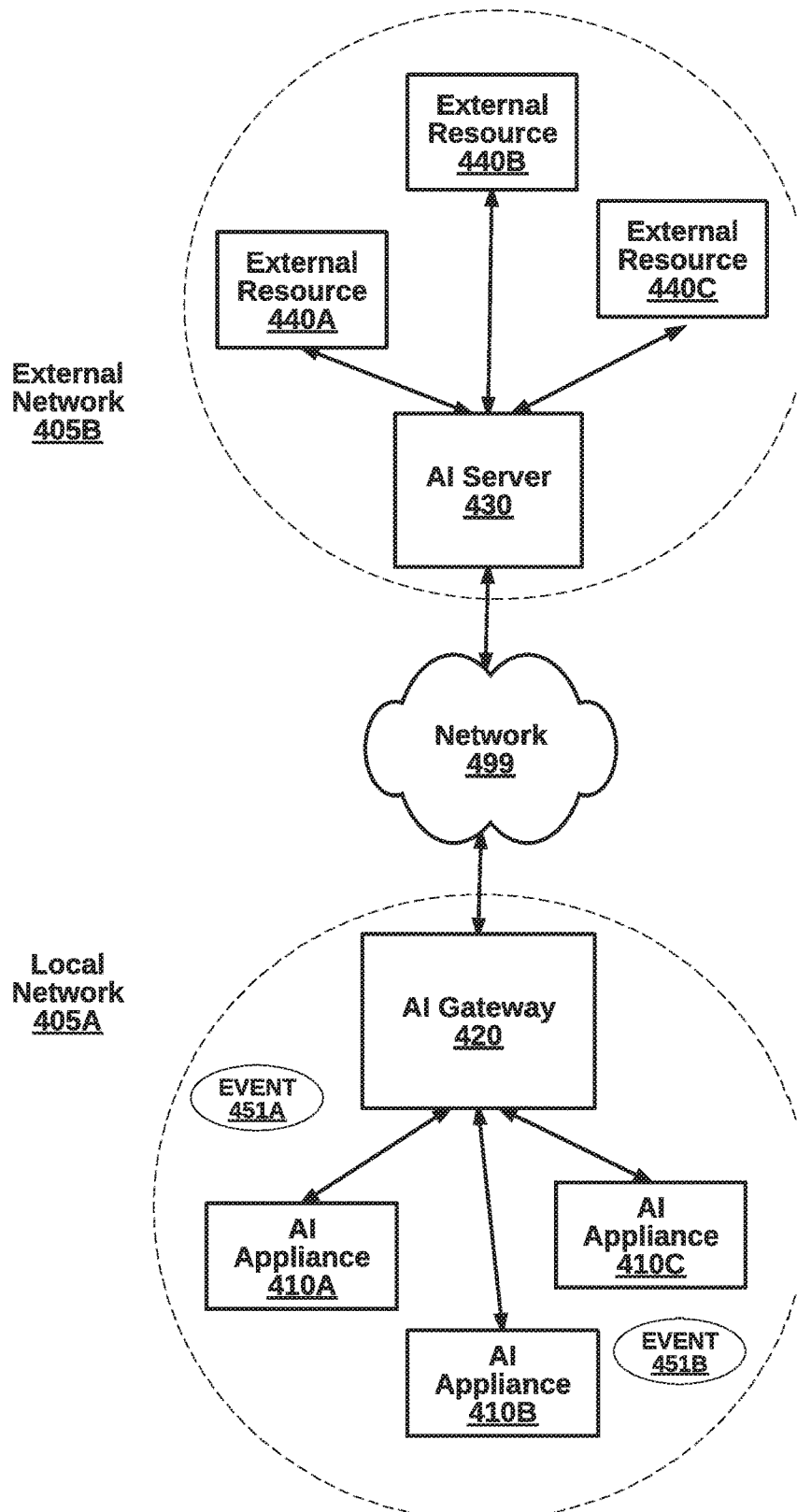
FIG. 4A is a high-level block diagram illustrating an example system for providing home automation using an external network, according to one embodiment.

FIG. 4A is a high-level block diagram illustrating a system 400A for providing home automation using an external network 405B, according to one embodiment. The system 400 comprises an internal network 405A coupled to the external network 405B via the network 499. The connections can be wired, wireless, or a combination of both using mediums such as the Internet, 3G/4G cellular networks, analog telephone lines, power lines, or the like.

The internal network 405A can represent a home, business, automobile, or combination of environments connected by a local area network (LAN) or another network. The internal network 405A includes AI appliances 410A-C and an AI gateway 420. The AI appliances 410A-C can be any consumer appliance or electronic device appropriate to integrate with the system 400. The AI appliances 410A-C in some embodiments are thin devices that rely on the AI gateway 420 for access to the external network 405B. Examples include wall plugs, over wall outlets, lamps, scones, switches, smoke detectors, home appliances (e.g., toasters and microwaves) and the like. More AI appliances and sensor improve AI performance. The AI gateway 420 accesses the external network 405B using, for example, a MAC card, a Bluetooth radio, an IEEE 802.11 wireless card, or the like. The AI gateway 420 can be a dedicated box, an application executing on a PC or network device, or an AI appliance acting as a master to other slave appliances. Also, the AI appliances 410A-C can be communicatively coupled in a mesh network, such that one AI appliance proxies as an access point for another. In another example, one device may have a Bluetooth connection only, and need to proxy through a device that is connected to the AI gateway 420 through an Ethernet connection.

The external network 405B can represent resources available through the network 499. The external network 405B includes AI server 430 and external resources 440A-C. The AI server 430 provides centralized management of the AI appliances 410A-C and processing of input from one or more sensors of one or more AI appliances 410A-C. The external resources 440A-C can be accessed by the AI server 430 on behalf of the AI appliances 410A-C. The external resources 440A-C can be, for example, online applications such as Pandora, Facebook, Google Search or Google Calendar.

In one example, event 451A is caused by a user requesting a calendar entry or song purchase from iTunes. The user is located proximate to the AI appliance 410A but may also be detected by audio sensors located further away on one of the other AI appliances 410B-C. The AI server 430 in this example, could geo-locate the user based on the amplitude of sound detection at the various sensors. With knowledge of a location, lights or other electronics can be activated in accordance with a user in that location. The AI server 430 could also recognize the user and activate electronics or trigger an event in a manner that is customized to a particular user.

In another example, event 451B is caused by an ambient condition such as a washing machine buzzer detected by one or more sensors. When a sound clip is received at the AI server 430, a local database or an external database can be searched in order to identify the event. Once identified, an appropriate event response can be executed. One event response can be a message displayed on a television detected as being on. Another event response can be an SMS message or an e-mail message that is automatically generated to include a description of the identified event and sent to a user.

The system 400A can have many variations, with more or less components, such as a system of AI appliances that are peers and share date between themselves, and AI appliances that are autonomous in that they individually connect to the AI server 430 or the external resources 440A-C. One implementation provides various levels of encryption. Another implementation includes a mobile user device (not shown) connected to the network 499, such as a smart phone, a tablet device, a laptop or even a stationary PC. The mobile device can be used as an additional AI appliance that interacts with the system 400 from within or outside of the environment. Additionally, sensor data and event feedback and confirmations can also be sent to the mobile device. Moreover, the system 400A can connect to outside AI systems (e.g., two different office locations, or a user's home and automobile).

Figure 4B:
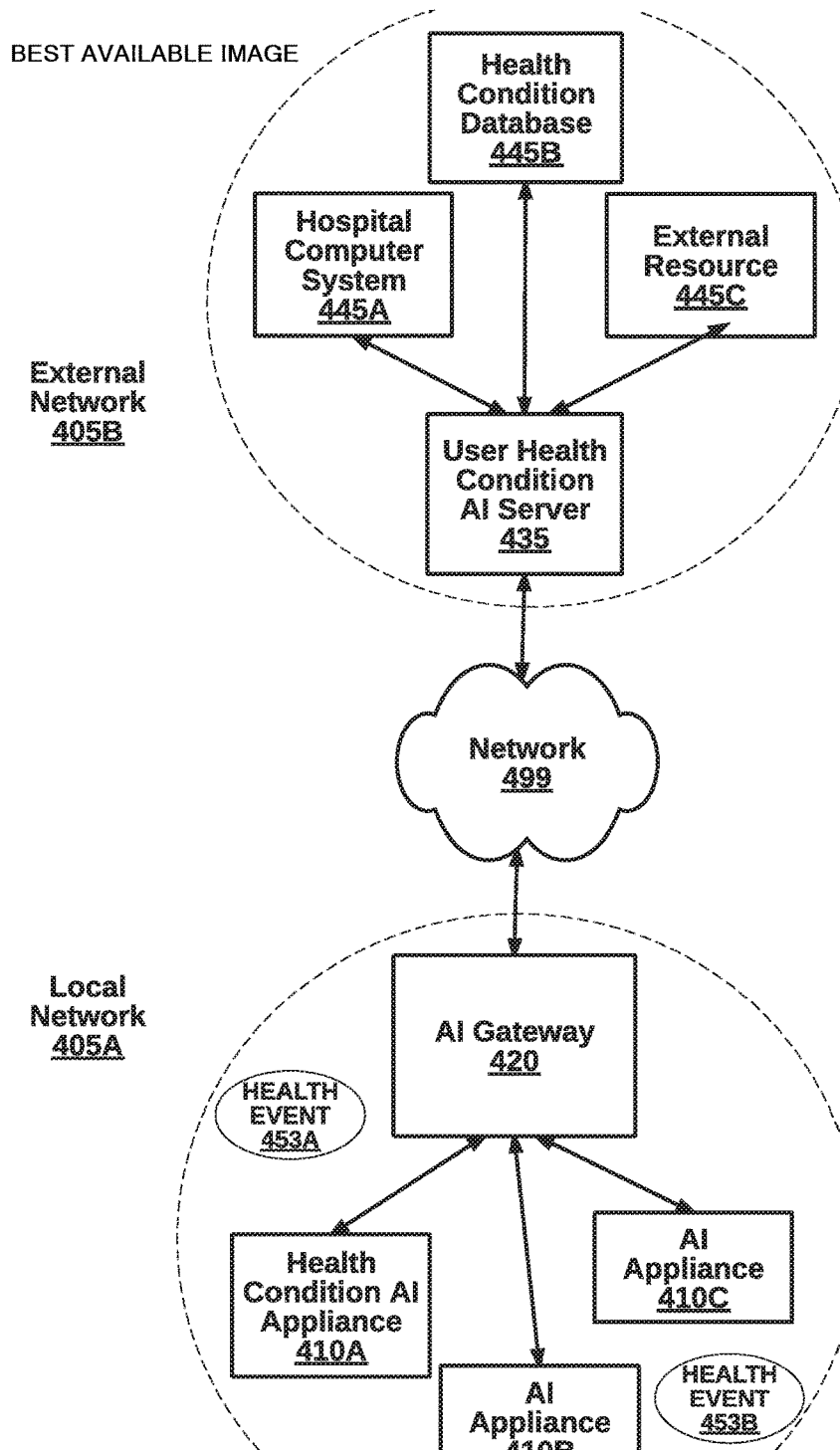
FIG. 4B is a high-level block diagram illustrating how call routes between multiple users over the example system of FIG. 4A, according to an embodiment.

FIG. 4B is a block diagram illustrating the specific application of health condition monitoring over the system 400A of FIG. 4A. The system 400B specifies a health condition AI server 435 along with a hospital computer system 445A and a health condition database 445B as examples of external resources for this particular embodiment of an AI server 430. Many other types of applications can be implemented alongside health condition monitoring, in some embodiments, and the system 400B can be a dedicated health condition monitoring system, in other embodiments.

The health condition AI server 435 uses geo-location of health events to provide feedback on diagnosed or predicted health conditions. In one case, a general AI server such as the AI server 430 is modified with software to add health condition monitoring to other functionality, and in another case, the health condition AI server 435 is a dedicated system.

The hospital computer system 445A can provide user specific data or doctor instructions to the health condition AI server 435. Based on progress from reports sent back to the hospital computer system 445A, the doctor can update user specific data. For example, an initial doctor instruction may be to listen for congestion while sleeping due to an asthma condition. The user is identified and tracked for indicators of sleep (e.g., user tracked to bedroom or couch, alarm is set, lights are turned off) and audio segments are collected with time stamps and measurements of intensity and duration. Once satisfied that the condition has subsided, asthma condition monitoring can be halted, or restricted, by the doctor. Many other examples are possible.

The health condition database 445B can provide configuration data and rules for various health conditions, and also habits that could lead to health conditions. One example is a database of probabilistic health models that can be updated with data and statistics as research evolves, for improved modeling. Another example of a health model updates as more data is collected from individuals of one or more AI systems. Data can be specific to geo-location (e.g., in cold room or in pet room), category, geography, demographics, or the like. Initially, a general set of health condition rules can be executed. As the health condition AI server 435 detects a threshold is met, then more specified health condition rules can be downloaded from the health condition database 445 for execution. In one implementation, observation of a cough from a particular user over a window in time, can result in an AI modification by downloading condition rules associated with cough, such as a cold, strep throat, and the like. In this manner, the probabilistic modeling of health conditions is adaptive. Other embodiments of adaptive probabilistic health modeling exist.

In one embodiment, the health condition AI server continually adapts by using the health condition database 445B to detect a certain health condition for a user, and then automatically interact with the hospital computer system 445A provide feedback to the user about how to address the health condition. The feedback can be in real-time and at a current location of the user.

A health condition AI appliance 410A can be a special purpose AI appliance or a modified AI appliance. Sensors that are specially configured for a particular health condition.

Figure 4C:
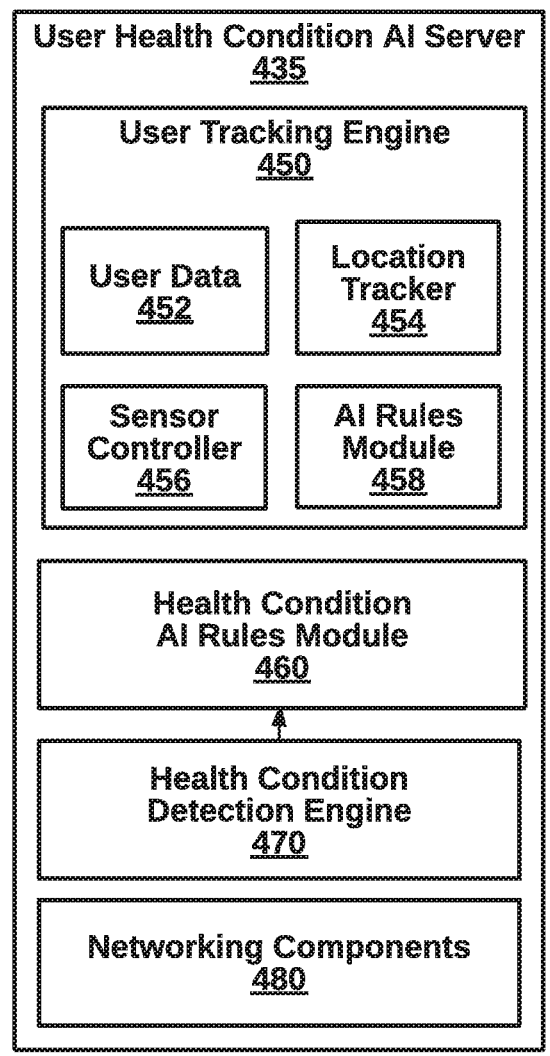
FIG. 4C is a more-detailed block diagram illustrating the user health condition AI server of FIG. 4B, according to an embodiment.

FIG. 4C is a more-detailed block diagram illustrating the user health condition AI server 435 of FIG. 4B, according to an embodiment. The user health condition AI server 435 includes a user tracking engine 450 for interacting in a customized way with multiple users. A health condition AI rules module 460 includes rules related to general or specific health conditions. Health condition rules can identify when an event is a health condition event, when health condition events amount to a diagnosis level or other level of concern, and can have parameters for a particular user, such as an ambient temperature instruction. A health condition detection engine 470 executes rules to detect health conditions. Networking components 480 includes the ports, antennae, networking protocols, transceivers, and the like, necessary for connecting to AI clients and external resources.

The user tracking engine 450 includes user data 452 to store identity profiles such as biometric voice data in association with registered users. A location tracker 454 triangulates or otherwise compares audio signals to determine location coordinates of each user. A sensor controller 456 registers AI clients and locations. An AI rules module 458 contains rules for general AI interactions, in contrast to the health condition AI rules module 460.

III. Methods for Providing Home Automation Using Sensors on AI Appliances

Figure 5:
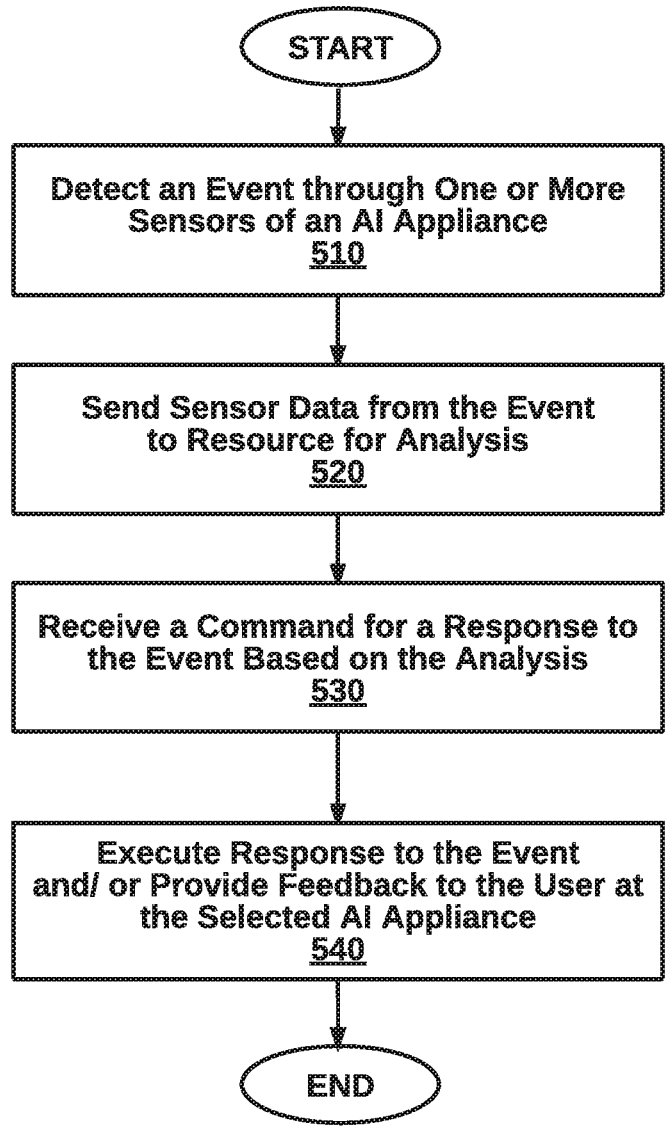
FIG. 5 is a flow diagram illustrating a method for providing home automation using an AI appliance, according to one embodiment.

FIG. 5 is a flow diagram illustrating a method 500 for providing home automation using an AI appliance, according to one embodiment. The method 500 can be implemented in any of the devices discussed above.

An event is detected through one or more sensors of an AI appliance (step 510). For instance, an audio sensor can have a volume threshold that defines an event once exceeded. A duration of an event can span an entirety of time that the volume remains about the threshold. The duration can also span a predetermined amount of maximum time. In some embodiments, constant or long-term sounds can be ignored or filtered. An event as defined by one sensor can define an event for another sensor. For example, if an audio event is detected, a bio sensor or temperature sensor can collect data over a corresponding duration, in order to provide a more robust response.

Sensor data is sent from the event to a resource for analysis (step 520). The analysis can occur at a local, or cloud-based server, or at a master AI appliance. The analysis interprets the event in order to determine an event response. A table or default or customized commands can be stored for correlating an identified event with a response sent back to an AI appliance. Certain events can be configured. For example, a new stove or alarm clock can be added through a user interface, causing a manufacturing download of sounds to be added to a database.

In some embodiments, an AI server accesses an external device for a query or other interaction with remote applications. Results can be sent back to the AI server or directly back to an AI appliance.

A command is received for a response to the event based on the analysis (step 530). The response to the event is executed and/or feedback is provided to the user, at the selected AI appliance (step 540). For example, an online music service is activated responsive to an event of a user asking for music. An LED light or voice can communicate a successful transaction. The music service can involve a first device while the LED light or voice feeds back at a second device, in some embodiments.

Figure 6:
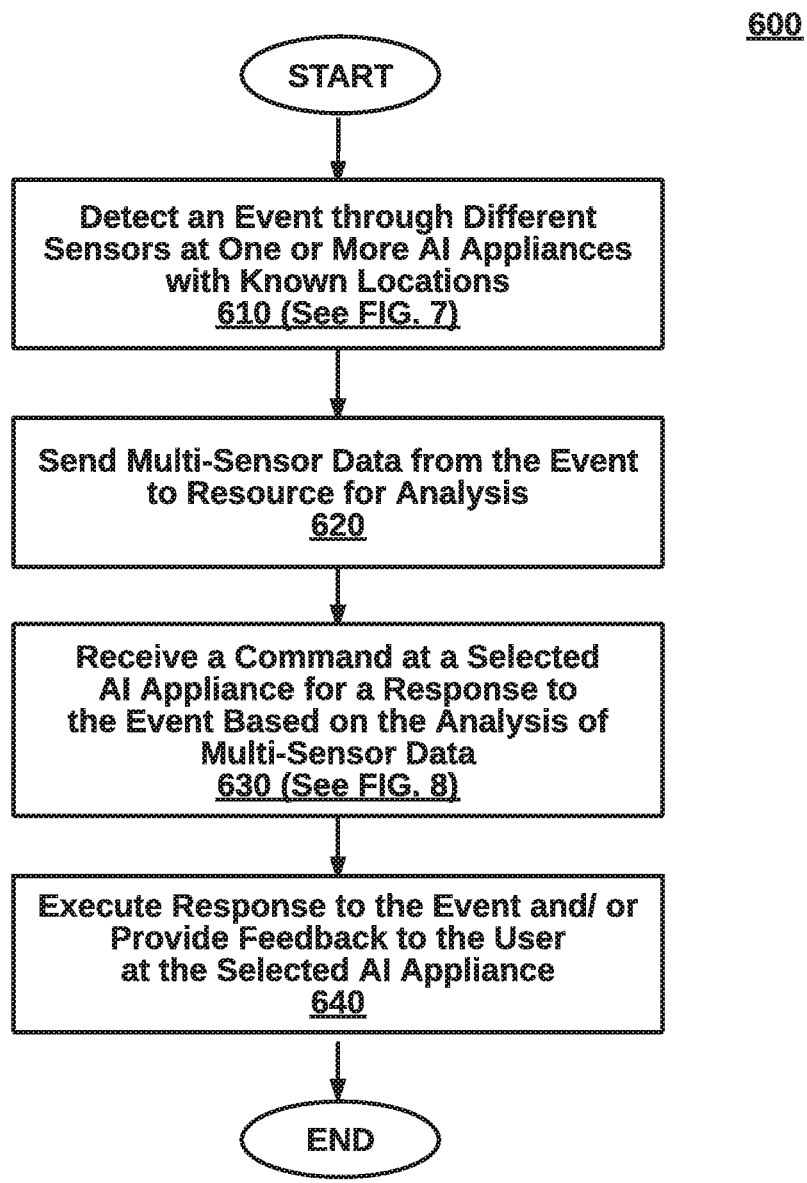
FIG. 6 is a flow diagram illustrating a method for coordinating multiple sensors to provide home automation using AI appliances, according to one embodiment.

FIG. 6 is a flow diagram illustrating a method 600 for coordinating multiple sensors to provide home automation using AI appliances, according to one embodiment.

An event is detected through different sensors at one or more AI appliances at a known location (step 610), as discussed in more detail below in association with FIG. 7. The locations can be preconfigured or determined using GPS, Wi-Fi triangulation, or other location technologies. In an embodiment, the layout of an environment including AI clients and other features (e.g., stairs, doors, bathrooms, etc.) are programmed by using a smartphone with location technology to take a location snapshot while also allowing a user to enter a description or scan a QR code or another identifier. The geographically-dispersed AI appliances are shown and discussed above in association with FIG. 3. The different sensors can also be embedded in a single device.

Multi-sensor data from the event is sent to a resource for analysis (step 620). The multiple perspectives afford a better characterization of events such as geo-location. A 3-dimensional data set forms from multiple inputs that traditional systems merely receive as linear data.

A command is received at a selected AI appliance for a response to the event based on the analysis of multi-sensor data, i.e., a response command (step 630), as discussed below and illustrated in FIG. 8. The response to the event is executed and/or feedback is provided to the user at the selected AI appliance (step 640), for example, at the detecting AI appliances or an application. The application can be embedded in an AI appliance or be a remotely located service (e.g., a cloud-based application).

Figure 7:
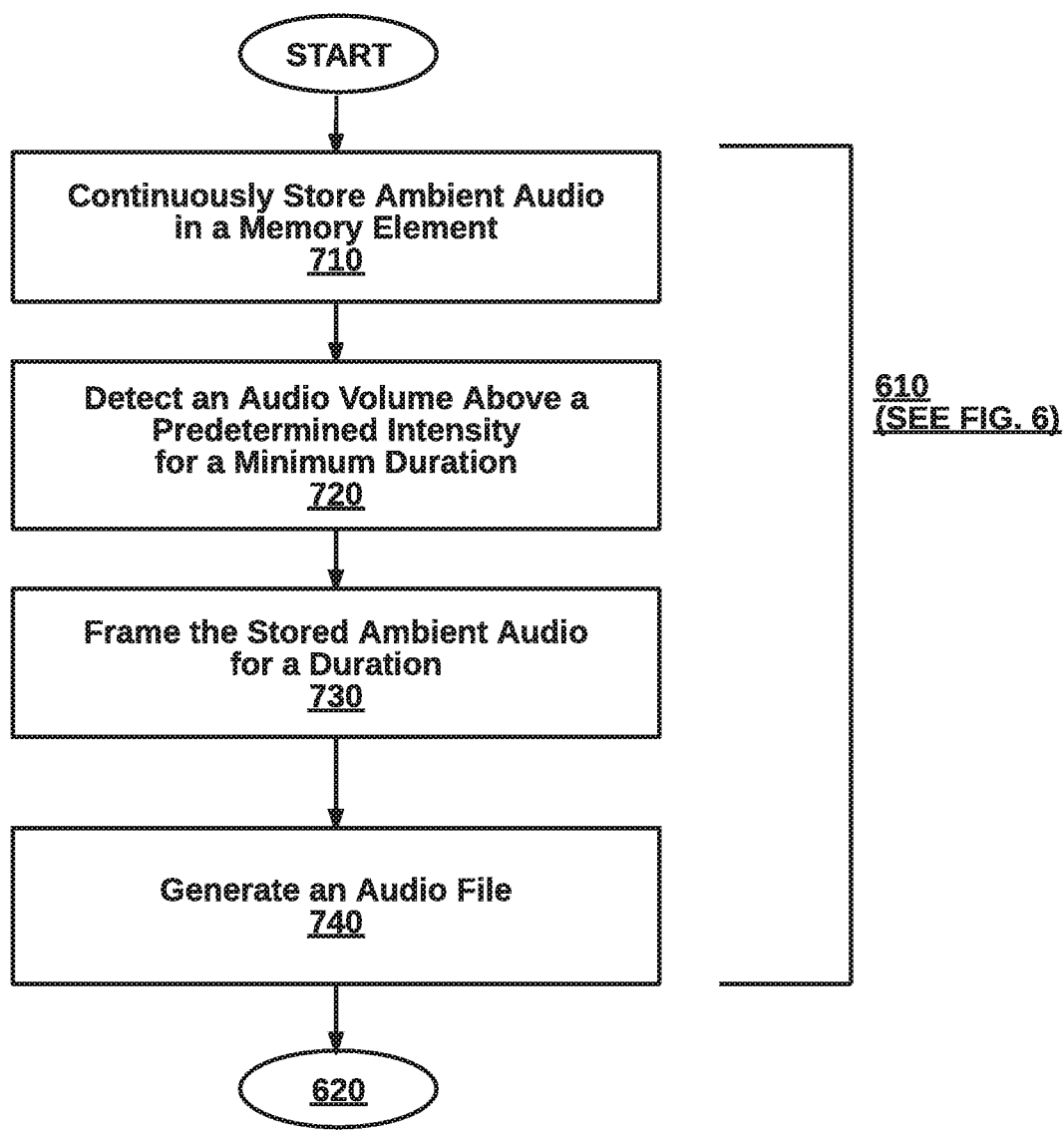
FIG. 7 is a more detailed flow diagram illustrating a step of detecting an event through different sensors at one or more AI appliances of the method of FIG. 6, according to one embodiment.

FIG. 7 is a more detailed flow diagram illustrating the step 610 of detecting an event through different sensors at one or more AI appliances of the method 600 of FIG. 6, according to one embodiment. Ambient audio is continuously stored in a memory element (step 710). An audio volume (or other characteristic) above a predetermine intensity for a minimum duration is detected (720), as indicative of a possible event. The stored ambient audio is framed for a certain duration (e.g., a duration above the predetermined intensity, or a sample thereof) (step 730). An audio file is generated from the framed ambient audio (e.g., compressed audio file suitable for network transmission) (step 740).

Figure 8:
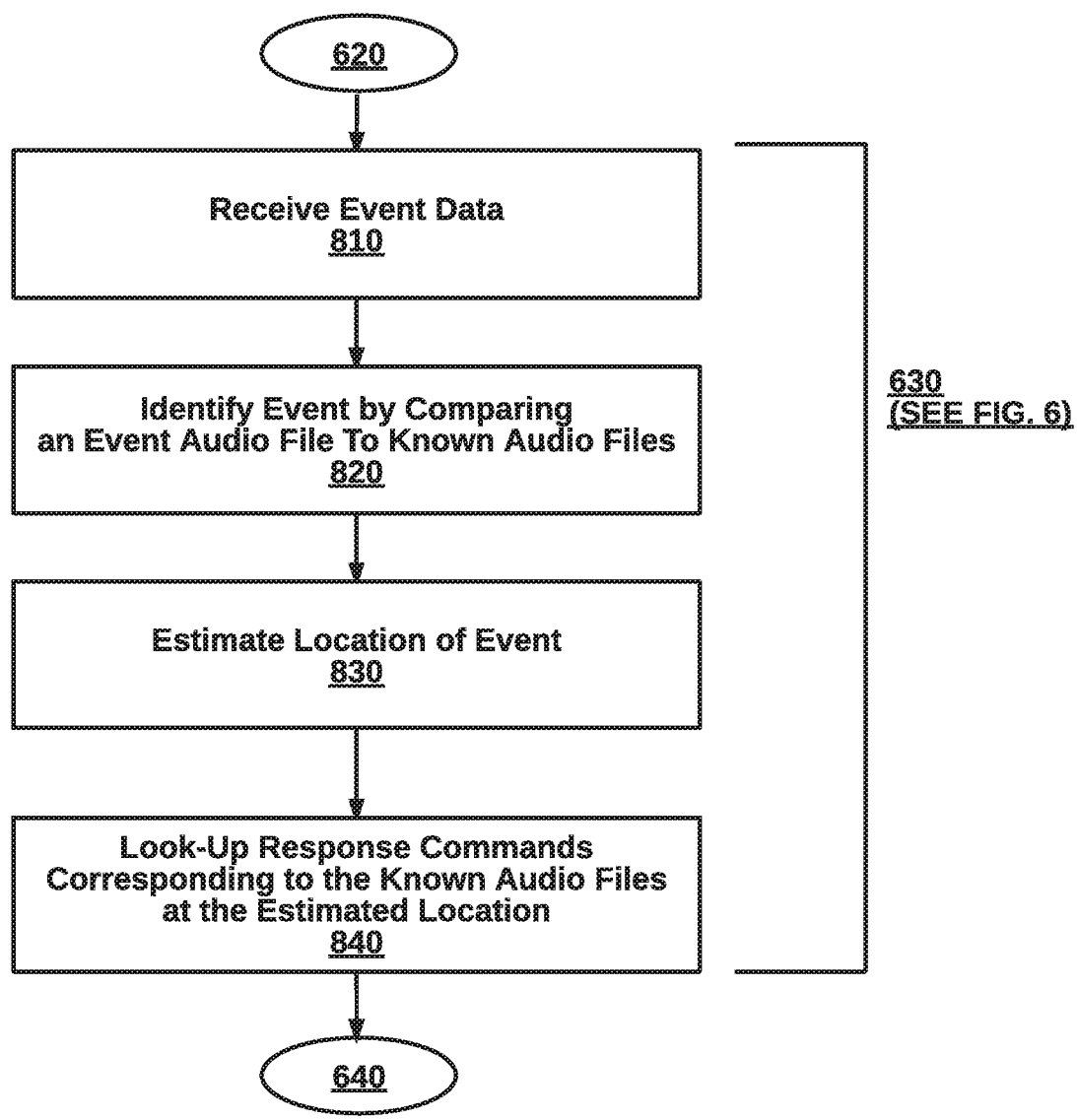
FIG. 8 is a more detailed flow diagram illustrating a step of analyzing multi-sensor data to determine a response command of the method of FIG. 6, according to one embodiment.

FIG. 8 is a more detailed flow diagram illustrating the step 630 of analyzing multi-sensor data to determine a response command of the method 600 of FIG. 6, according to one embodiment. Event data is received (step 810). An event is identified from the event data by comparing an event audio file to a table or records of known audio files (step 820). A location of the event is estimated (step 830). Finally, a response command corresponding to known audio files in view of the estimated location is looked-up (step 840)

Figure 9:
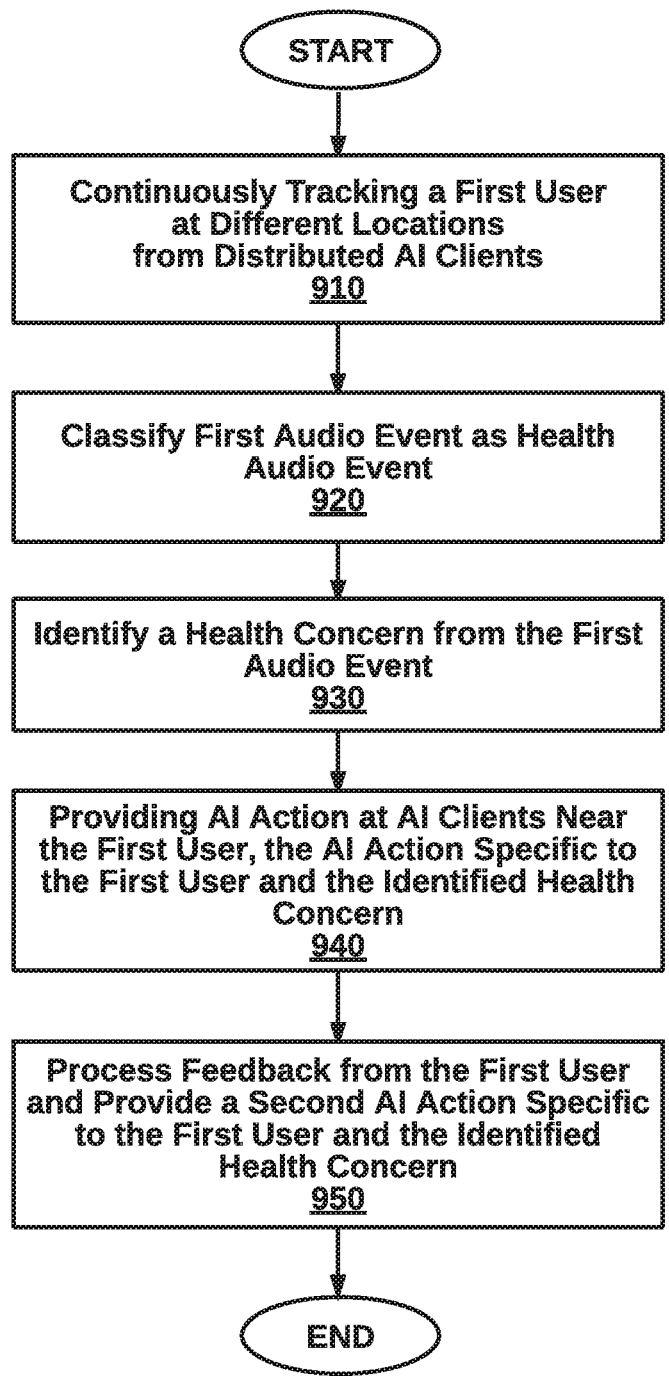
FIG. 9 is a flow diagram illustrating an example of providing home automation by using AI appliances for monitoring health conditions of users within an AI environment, according to one embodiment.

FIG. 9 is a flow diagram illustrating an example method for providing home automation by using AI appliances for monitoring health conditions of users within an AI environment, according to one embodiment.

Location information for AI clients is stored (step 910). Each AI client can self-report a location once affixed to an outlet or another base. In another embodiment, a scanner with GPS capability can report locations by scanning an AI client for identification and attaching location data for uploading. Alternatively, a network administrator can provide or link a database of locations in association with AI client identifications.

Audio event data that has been detected for a user is classified as a health audio event (step 920). A processor determines that the audio event data comprises a health audio event (i.e., either due to the audio event alone, or due to a combination of benign audio events in combination) that should be tracked. As described above, sensor data from a detected health event can be sent to a resource for analysis (e.g., an AI gateway). Based on the analysis, a command is sent for execution at a selected AI client. In one case, the AI clients can warm a user against eating certain foods after a certain time when the user is detected it he kitchen. In another case, user can also be partially woken up responsive to activity during sleep. In still another case, emergency service and relatives can be contacted if a trip and fall or scream for help is detected.

A health concern can be identified at a server from the health audio event (step 930). The health concern may be identified for the first time, or can already be under monitoring.

In response, an AI action is provided at AI clients near the first user (step 940). The AI action is specific to the identified health concern, even if the command is just a reminder to drink water. In one case, the audio feedback comes from more than one AI client, and the audio level of each AI client depends on the spatial location of a user between the AI clients. The audio feedback can be to the same location as the detected audio health event, or at an updated location if the user has moved.

In some cases, a user gives feedback in response to the AI client feedback (step 950). A second AI section specific to the user, the health concern, and the user feedback can be processed and performed, in some embodiments. For example, if a user is reminded to take a medication, the user may inform the home automation system that a refill is needed. In turn, the home automation system may order a refill to be mailed at a hospital server, and advise the user of a delivery date.

IV. Generic Computing Device (FIG. 10)

Figure 10:
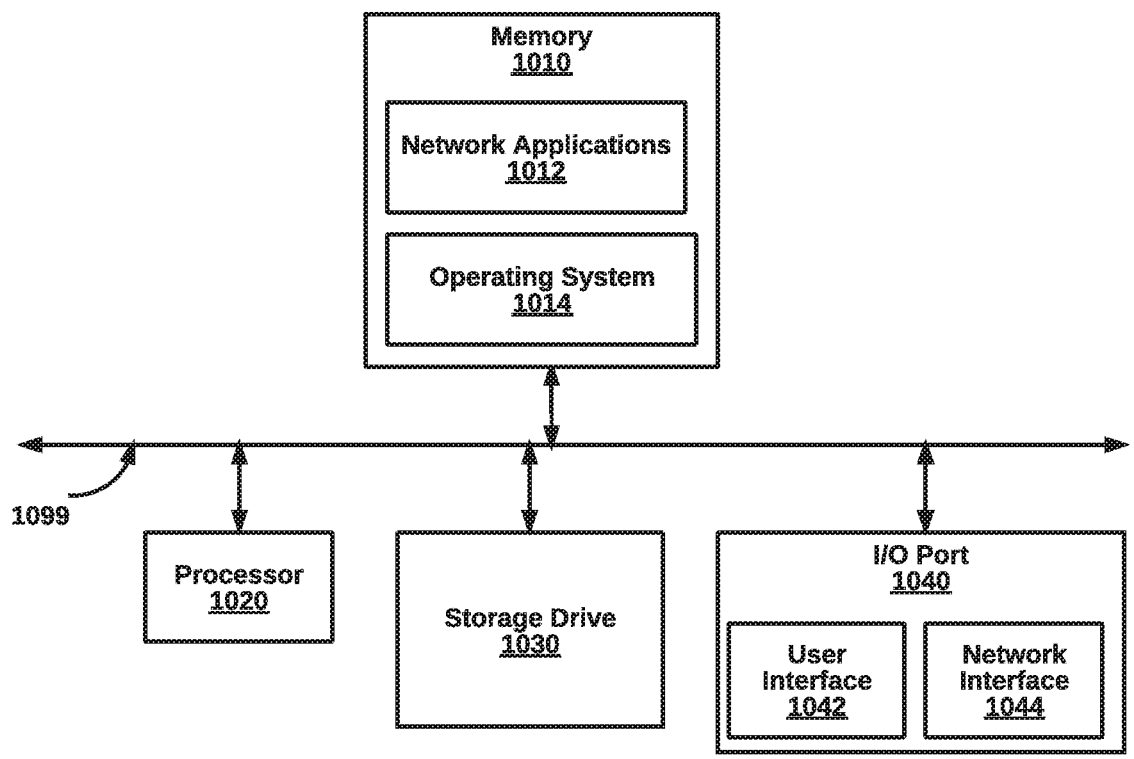
FIG. 10 is a block diagram of an exemplary computing device, according to one embodiment.

FIG. 10 is a block diagram illustrating an exemplary computing device 1000 for use in the system 400 of FIG. 4, according to one embodiment. The computing device 1000 is an exemplary device that is implementable for each of the components of the system 100, including the AI gateway 420 and the AI server 410. The computing device 1000 can be a mobile computing device, a laptop device, a smartphone, a tablet device, a phablet device, a video game console, a personal computing device, a stationary computing device, a server blade, an Internet appliance, a virtual computing device, a distributed computing device, a cloud-based computing device, or any appropriate processor-driven device.

The computing device 1000, of the present embodiment, includes a memory 1010, a processor 1020, a storage drive 1030, and an I/O port 1040. Each of the components is coupled for electronic communication via a bus 1099. Communication can be digital and/or analog, and use any suitable protocol.

The memory 1010 further comprises network applications 1012 and an operating system 1014. The network applications 1020 can be the AI gateway 420 or the AI server 430, for example. Other network applications 1012 can include a web browser, a mobile application, an application that uses networking, a remote application executing locally, a network protocol application, a network management application, a network routing application, or the like.

The operating system 1014 can be one of the Microsoft Windows® family of operating systems (e.g., Windows 99, 98, Me, Windows NT, Windows 2000, Windows XP, Windows XP x64 Edition, Windows Vista, Windows CE, Windows Mobile, Windows 9 or Windows 8), Linux, HP-UX, UNIX, Sun OS, Solaris, Mac OS X, Alpha OS, AIX, IRIX32, or IRIX64. Other operating systems may be used. Microsoft Windows is a trademark of Microsoft Corporation.

The processor 1020 can be a network processor (e.g., optimized for IEEE 802.11), a general-purpose processor, an application-specific integrated circuit (ASIC), a field programmable gate array (FPGA), a reduced instruction set controller (RISC) processor, an integrated circuit, or the like. Qualcomm Atheros, Broadcom Corporation, and Marvell Semiconductors manufacture processors that are optimized for IEEE 802.11 devices. The processor 1020 can be single core, multiple core, or include more than one processing elements. The processor 1020 can be disposed on silicon or any other suitable material. The processor 1020 can receive and execute instructions and data stored in the memory 1010 or the storage drive 1030.

The storage drive 1030 can be any non-volatile type of storage such as a magnetic disc, EEPROM, Flash, or the like. The storage drive 1030 stores code and data for applications.

The I/O port 1040 further comprises a user interface 1042 and a network interface 1044. The user interface 1042 can output to a display device and receive input from, for example, a keyboard. The network interface 1044 (e.g. RF antennae) connects to a medium such as Ethernet or Wi-Fi for data input and output.

Many of the functionalities described herein can be implemented with computer software, computer hardware, or a combination.

Computer software products (e.g., non-transitory computer products storing source code) may be written in any of various suitable programming languages, such as C, C++, C #, Oracle® Java, JavaScript, PHP, Python, Perl, Ruby, AJAX, and Adobe® Flash®. The computer software product may be an independent application with data input and data display modules. Alternatively, the computer software products may be classes that are instantiated as distributed objects. The computer software products may also be component software such as Java Beans (from Sun Microsystems) or Enterprise Java Beans (EJB from Sun Microsystems).

Furthermore, the computer that is running the previously mentioned computer software may be connected to a network and may interface to other computers using this network. The network may be on an intranet or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, and 802.11ac, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

V. Additional Embodiments

Many additional techniques are possible in conjunction with the system described herein. One technique concerns set-up. Once out of the packaging, accounts are configured for the system 100 (e.g., on the AI gateway 420), and partner accounts are set-up for compatibility. AI clients are plugged into the wall, lamps, and otherwise, at geographically dispersed locations. Once paired with an access point or home router, a human voice interface can guide set-up at one or any of the AI clients, or optionally through a PC. Natural conversation is preferably used for set up by asking the user questions, such as "What room am I in?", "Who am I talking to?", "Are any other users around?", "What was the cause of that loud noise?" Biometric identifications are generated from voice and other ambient conditions (e.g., walking sound, coughing, etc.). Responses allow unique biometric information to be collected for identification of users at a different time. Each individual AI can be set-up, along with a system-wide set-up and calibration.

Another technique involves different AI interfaces based from an AI device inside the network, a network edge, and from the cloud. There can be many, separate human voice interfaces, with independent processes and preferences. Different human voice interfaces can serve the system as a whole, each user, each AI appliance, or each service (e.g., telephone calls). For example, an interface named Alice with a distinctive voice can track a specific user around the system, and other users can adapt to tune out Alice's voice. Information can be kept to a particular interface or submitted for global use. AI appliances on the edge, such as user telephone when away from home, or a smart car can also have unique interface actions.

Yet another technique provides a hub for all external AI services. In more detail, the system can analyze a request and match the request to an AI system or non-AI system having the appropriate capability to respond the request (e.g., Alexa, Google Now, Google Search, Viv, Siri, and Cortana). In one case, if an instant message is requested to be sent to a friend, the system can recognize that Facebook Messenger is the preferred or only communication channel between the two friends. The voice sample is translated to text and then encapsulated using a Facebook Messenger API and sent to a Facebook gateway for further processing. An acknowledgment of success can be sent back downstream and output from a nearby AI device.

Additionally, a dynamic ambient condition sensor can modify actions of the system based on context. This allows each interaction with a user to be unique and optimized. Knowing condition of the room and the identity of the user prior to feedback improves the timing, mechanism, intensity, and the like for feedback. Conditions can also include noise level, amount of light, other nearby users, temperature, other system activities, and more. For instance, feedback in a living room with a loud television at 2 PM can be different from feedback in a baby room at 2 AM.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

We claim:

1. A computer-implemented method in an AI (artificial intelligence) server of an (AI) system for automatically monitoring health conditions by continuously tracking users identified by the AI server with a plurality of AI clients implemented in hardware, the method comprising the steps of:

storing location information for each of the plurality of AI clients, each of the AI clients comprising an audio sensor, a network controller, and a feedback mechanism within a common enclosure, and the plurality of AI clients being geographically-dispersed;

responsive to an explicit identification of at least a first user of a plurality of users to any of the AI clients, collecting identity information associated with the individual user for an identification profile of a plurality of identification profiles, the identity information comprising biometric data and non-biometric data;

detecting a first audio event and identity data at a first location at a first time that is received by at least a first AI client of the plurality of AI clients;

identifying the first user out of the plurality of users as being associated with the first audio event;

classifying the first audio event as a first health audio event based on other audio events taken in combination with the first health audio event and occurring within a window of time;

responsive to continuously tracking events of the first user over time as locations dynamically change based on subsequently detected audio events, determining that at least one health concern of the user has reached a threshold level compared against a baseline of a probabilistic health model; and providing a first AI action concerning the first user based on the determined health concern.

2. The method of claim 1, the step of audio event classification comprises:

classifying the first audio event as the first health audio event including comparing the audio event and the first location against one or more specific health concerns associated with the first user and/or the first location.

3. The method of claim 1, further comprising:

receiving input during the identity information collection indicating the one or more specific health concerns; and associating the one or more specific health concerns with the first user.

4. The method of claim 1, wherein the step of audio event classification comprises:

classifying the audio event as a health audio event including comparing the audio event general health concerns; and automatically associating one or more general health concerns with the first user as the one or more specific health concerns.

5. The method of claim 1, wherein the step of at least one health concern determination comprises:

determining that at least one health concern of the user has reached a threshold level based on a combination of health audio events compared against a baseline of a probabilistic health model.

6. The method of claim 1, wherein continuously tracking events comprises continuously tracking health events as locations dynamically change.

7. The method of claim 1, wherein the at least one health concern determination comprises:

determining that at least one health concern of the user has reached a threshold level based on a combination of health audio events of different types compared against a baseline.

8. The method of claim 1, wherein the health audio event comprises one or more of: a cough, a sneeze, a sniffle, a snore, a gate, a voice, a bathroom visit, a vomit, a refrigerator visit, food preparation, a fall, a crash, panic, a cry or a scream.

9. The method of claim 1, wherein the step of providing the first AI action comprises:

providing audio and/or visual feedback concerning at least the first health event at a current location of the first user.

10. The method of claim 1, wherein the audio and/or visual feedback is provided in real-time with a detected health audio event.

11. The method of claim 1:

wherein collecting identification information comprises collecting biometric identification information associated with the individual user, and wherein determining that that the audio event data originates from the first user comprises classifying the audio event data by comparing the audio event data against at least the biometric identification information.

12. The method of claim 1:

wherein collecting identification information comprises collecting non-biometric information originating from the individual user interacting with one or more physical objects, and wherein determining that that the audio event data originates from the first user comprises classifying the audio event data by comparing the audio event data against at least the non-biometric information using a probabilistic model.

13. The method of claim 1, wherein the estimated locations of the first user and the second user are determined without attached location devices.

14. The method of claim 1, wherein the step of first audio event detection includes determining a location based on audio detected at least two of the plurality of AI clients.

15. The method of claim 1, wherein the first audio event is not considered a health audio event when considered in isolation.

16. The method of claim 1, wherein the location is determined by relative sound intensity at more than one AI client.

* * * * *